(12) United States Patent
Agarwal et al.

(10) Patent No.: US 10,318,833 B2
(45) Date of Patent: Jun. 11, 2019

(54) SYSTEM AND METHOD FOR PERSON IDENTIFICATION AND PERSONALITY ASSESSMENT BASED ON EEG SIGNAL

(71) Applicants: Puneet Agarwal, New Delhi (IN); Siddharth Panwar, New Delhi (IN)

(72) Inventors: Puneet Agarwal, New Delhi (IN); Siddharth Panwar, New Delhi (IN); Shiv Dutt Joshi, New Delhi (IN); Anubha Gupta, New Delhi (IN)

( * ) Notice: Subject to any disclaimer, the term of this patent is extended or adjusted under 35 U.S.C. 154(b) by 0 days.

(21) Appl. No.: 15/544,004

(22) PCT Filed: Jan. 18, 2016

(86) PCT No.: PCT/IB2016/050227
§ 371 (c)(1),
(2) Date: Jul. 16, 2017

(87) PCT Pub. No.: WO2016/113717
PCT Pub. Date: Jul. 21, 2016

(65) Prior Publication Data
US 2018/0025241 A1    Jan. 25, 2018

(30) Foreign Application Priority Data
Jan. 16, 2015 (IN) .......................... 2007/DEL/2014

(51) Int. Cl.
*G06K 9/00* (2006.01)
*A61B 5/00* (2006.01)
(Continued)

(52) U.S. Cl.
CPC ...... *G06K 9/00885* (2013.01); *A61B 5/04012* (2013.01); *A61B 5/0476* (2013.01); *A61B 5/0478* (2013.01); *A61B 5/117* (2013.01); *A61B 5/167* (2013.01); *A61B 5/7239* (2013.01); *G06K 9/00496* (2013.01); *G06K 9/00523* (2013.01); *G06K 9/00536* (2013.01); *G06K 9/6214* (2013.01); *A61B 5/7246* (2013.01); *A61B 5/7257* (2013.01); *G06K 2009/00939* (2013.01); *G06K 2009/00953* (2013.01); *G06K 2209/05* (2013.01)

(58) Field of Classification Search
CPC ............ G06K 9/00885; G06K 9/6214; G06K 9/00536; G06K 9/00523; G06K 9/00496; G06K 2209/05; G06K 2009/00953; G06K 2009/00939; A61B 5/04012; A61B 5/167; A61B 5/0478; A61B 5/117; A61B 5/0476; A61B 5/7239; A61B 5/7246; A61B 5/7257
USPC ......................................................... 382/115
See application file for complete search history.

(56) References Cited

U.S. PATENT DOCUMENTS

4,736,751 A * 4/1988 Gevins ................. A61B 5/0017
600/544
7,594,122 B2   9/2009 Milgramm et al.
(Continued)

*Primary Examiner* — Jerome Grant, II (57) ABSTRACT

The present invention relates a novel system and method for person identification and personality assessment based on electroencephalography (EEG) signal. More particularly, this invention relates to a novel method of EEG recording and processing to map the inherent and unique properties of brain in the form of highly specific brain signature to be used as means for person identification and personality assessment.

17 Claims, 6 Drawing Sheets

(51) Int. Cl.
*A61B 5/0476* (2006.01)
*A61B 5/117* (2016.01)
*A61B 5/04* (2006.01)
*A61B 5/0478* (2006.01)
*A61B 5/16* (2006.01)
*G06K 9/62* (2006.01)

(56) References Cited

U.S. PATENT DOCUMENTS

| | | | |
|---|---|---|---|
| 2006/0251303 A1* | 11/2006 | He | A61B 5/04008 |
| | | | 382/128 |
| 2006/0287607 A1* | 12/2006 | Sackellares | G05B 23/024 |
| | | | 600/544 |
| 2011/0306895 A1* | 12/2011 | Nakashima | A61B 5/04017 |
| | | | 600/544 |
| 2012/0289854 A1* | 11/2012 | Yamada | G01R 33/4806 |
| | | | 600/544 |
| 2014/0020089 A1 | 1/2014 | Perini, II | |
| 2014/0188770 A1 | 7/2014 | Agrafioti et al. | |
| 2014/0254939 A1* | 9/2014 | Kimura | H04N 5/23219 |
| | | | 382/201 |
| 2014/0376794 A1* | 12/2014 | Dumoulin | G01R 33/5611 |
| | | | 382/131 |
| 2015/0371390 A1* | 12/2015 | Gassner | G06T 7/10 |
| | | | 382/128 |
| 2017/0215968 A1* | 8/2017 | Rodriguez-Ponce | |
| | | | G16H 50/50 |
| 2017/0367607 A1* | 12/2017 | Agarwal | A61B 5/0476 |

\* cited by examiner

|   | 1 | 2 | 3 | 4 | 5 | 6 | 7 | 8 | 9 |    |
|---|---|---|---|---|---|---|---|---|---|----|
| 1 | 1013.035 | 772.4686 | 1010.943 | 1306.416 | 1069.249 | 1126.309 | 994.4431 | 962.749 | 983.8137 | Cz |
| 2 | 772.4686 | 930.7475 | 958.2692 | 1371.434 | 905.3931 | 1029.344 | 750.9833 | 836.0429 | 786.7128 | Fp2 |
| 3 | 1010.943 | 958.2692 | 1322.706 | 1629.754 | 1301.435 | 1363.969 | 1143.631 | 1096.675 | 1115.698 | F4 |
| 4 | 1306.416 | 1371.434 | 1629.754 | 2368.216 | 1694.967 | 1831.514 | 1461.635 | 1495.445 | 1403.401 | F8 |
| 5 | 1069.249 | 905.3931 | 1301.435 | 1694.967 | 1685.329 | 1566.096 | 1451.442 | 1331.021 | 1412.942 | C4 |
| 6 | 1126.309 | 1029.344 | 1363.969 | 1831.514 | 1566.096 | 1734.303 | 1450.451 | 1422.764 | 1381.981 | T4 |
| 7 | 994.4431 | 750.9833 | 1143.621 | 1461.635 | 1451.442 | 1450.451 | 1612.988 | 1361.478 | 1497.77 | P4 |
| 8 | 962.749 | 836.0429 | 1096.675 | 1495.445 | 1331.021 | 1422.764 | 1361.478 | 1559.591 | 1265.041 | T6 |
| 9 | 983.8137 | 786.7128 | 1115.698 | 1403.401 | 1412.942 | 1381.981 | 1497.77 | 1265.041 | 1617.378 | O2 |
|   | Cz | Fp2 | F4 | F8 | C4 | T4 | P4 | T6 | O2 |    |

SYSTEM AND METHOD FOR PERSON IDENTIFICATION AND PERSONALITY ASSESSMENT BASED ON EEG SIGNAL

FIELD OF THE INVENTION

The present invention relates a novel system and method for person identification and personality assessment based on electroencephalography (EEG) signal. More particularly, this invention relates to a novel method of EEG recording and processing to map the inherent and unique properties of brain in the form of highly specific brain signature to be used as means for person identification and personality assessment.

BACKGROUND OF THE INVENTION

There are available various biometric systems that use the human inherent physiological or behavioral characteristics for personal identification. The biometric system works on physical characteristics and behavioral characteristics kind. Physical characteristics are innate, congenital human physical characteristics, such as fingerprints, iris, hand geometry; face, etc. have genetic virtue. Behavior is performed from a person's motion features extracted, mostly acquired, such as handwriting, keystroke, gait, etc. Biometrics is considered as one of the technologies that changed the world and as expected in the near future, biometric authentication technology will delve into all aspects of our lives, and its influence will be integrated as much as the Internet.

Everyone has a biometric different from others in uniqueness and stability in the same period of time, not easy to forgery and counterfeiting, so the use of biometrics for identity finds a safe, reliable, and accurate. However, no single biometric is perfect, and various biometric identification methods have its certain scope and requirements of a single biometric system in practical applications show their limitations. The reliability of fingerprint identification is relatively high but requires actual physical contact; human face and iris recognition does not require physical contact, but in practice theft applications are subject to more environmental restrictions. Studies have shown that using gelatin fake finger can easily fool the fingerprint recognition system, the iris of people suffering from cataracts will change. With the continuous criminal means, intelligent, science and technology, the biometric system has security challenges.

In comparison with biometric identification method an EEG identification method is a relatively new idea. In fact, as early as in 1960s, neurophysiologists and psychiatrists proposed and validated "human EEG carries genetic information and the existence of a correlation between them". However, most of the early research is committed to pathological analysis and clinical diagnostics; until recent years, researchers have only put more energy into the health of the human body, trying to establish some sort of individual characteristics and their EEG carries genetic information which will serve as an effective EEG characteristic for identification.

It is proven that the EEG signals based biometric systems can achieve a certain accuracy and faster speed, and does not produce any harm to the human body. Since EEG signals are basically the brain's thinking activity, it is difficult to counterfeit. The human brain EEG analysis shows that different individuals in different brain regions will produce different neural impulse response and hence it is individual specific.

However, there is a common problem with normal EEG data processing. EEG usually reflects thousands of simultaneous on-going brain processes. EEG is still interpreted as two dimensional in clinical practice plotting voltage values in relation to time which does not reveal any unique quality of an individual. The brain response to a single stimulus or event of interest is not usually visible in the EEG recording of a single trial. In order to view the brain response to a specific stimulation applied to a subject under study, multiple trials (i.e. 100 trials or more) must be conducted to cause random brain activity to be averaged out and hence to remain the relevant ERP. Furthermore, multi-trial averaging contributes to loss of distinctive physiological information, which may prove useful for individual identification, disease diagnosis, and other fields of study such as psychology and pharmaceuticals. As such, an estimation scheme based on a single trial, which uses new signal processing EEG techniques, minimizes the information loss and reduces ERP or EP recording time is highly desirable.

The importance of accurate, timely detection of brain activity is crucial if to be used in identification and authentication. However, most mental and neurological states are evaluated mainly through interviews and subjective exams based on the subjects' temporary performance at that time. There is no objective quantitative test for evaluating baseline brain function. Imaging technologies such as standard magnetic resonance imaging (MRI) show only structure within the brain without providing an indication of dynamic brain function. Magnetic resonance spectroscopy and functional MRI provide functional status of different regions of brain but their use is very limited due to high cost, non-portability and limited availability of machines. EEG is the most effective, accurate and cheap method for evaluating brain function, but interpretation requires interpretation of multichannel graphs based on visual analysis by highly trained experts. Moreover current interpretation of EEG by expert does not provide any individual identification or early disease prediction due to lack of use of advanced signal processing techniques.

The present invention overcomes the above shortcomings by providing a novel methodology, which will be helping in diagnosing the different brain activity more accurately and comprehensibly as a brain signature. The matrix formed using EEG data will characterize the unique features of an individual, which can be used as person identification and assessment.

OBJECT OF THE INVENTION

The main object of the present invention is to provide a novel system and method for person identification and personality assessment based on electroencephalography (EEG) signals.

Yet another object of the present invention is to provide a novel method of EEG recording and processing to map the inherent unique properties of brain in the form of highly specific brain signature.

Yet another object of the present invention is to provide a novel system based on EEG which can be used as person identification.

Yet another object of the present invention is to provide a novel system based on EEG which can be used for personality assessment.

Yet another object of this invention is to provide a novel method of EEG recording and processing.

Yet another object of this invention is to identify the individual in a novel manner.

Yet another object of this invention is to perform EEG analysis that further includes statistical, temporal and spectral property assessment of the EEG signals through four dimensional visualisation of eigenvectors/eigenvalues, and properties of inner product spaces plotted with time.

Yet another object of this invention is to perform EEG wherein multiple output data resulting from recorded EEG patterns are taken together and the structure of their correlation and higher-order statistics matrices are analyzed in relation to time through its eigenvalues, eigenvector, eigendirection and eigenspaces and other signal processing techniques like fast Fourier transform compression sensing, wavelet transform to obtain said four dimensional activity.

Yet another object of this invention is to analyze the EEG recording using eigenvalues, eigenvectors, eigendirections and eigenspaces.

Yet another object of this invention is to use the Spinal EEG and its analysis to predict different diseases as well as source of EEG signals.

Yet another object of this invention is to create and use 4 dimensional EEG images.

Still another object of this invention is to record EEG from the surface of the brain bypassing the skull bone for diagnosing specific brain activity.

SUMMARY OF THE INVENTION

Accordingly, the present invention relates a novel system and method for person identification and personality assessment based on electroencephalography (EEG) signal. More particularly, this invention relates to a novel method of EEG recording and processing to map the inherent and unique properties of brain in the form of highly specific brain signature to be used as means for person identification and personality assessment.

In a preferred embodiment of the present invention eigenvectors/eigenvalues, properties of inner product spaces and 4D visualization of EEG signal's statistical, temporal and spectral properties is proposed to assess and interpret brain signature and personality of a subject. The proposed system analyses the EEG signals and giving values for three parameters each for left and right side of the brain, namely, $\rho$, $\theta$, and h, which represent the underlying mathematical structure of the signals appearing on the scalp. The three parameters are then plotted with time to give the novel 4 dimensional visualization of the entire EEG activity of the brain.

In another preferred embodiment of the present invention, a biometric kit for EEG based identification of person and/or personality assessment of a user is proposed. The kit comprises a means for data input, a processing unit, and an output device. Characterized in that, the processing unit provides 4 dimensional visualization of brain activity resulting into projection of brainwave based signature.

BRIEF DESCRIPTION OF DRAWINGS

A complete understanding of the device and system of the present invention may be obtained by reference to the following drawings:

FIG. 4 shows 9×9 covariance matrix of the data obtained in FIG. 3.

FIG. 5 shows the 9 eigenvectors, with corresponding eigenvalues of the matrix in FIG. 4.

DETAILED DESCRIPTION OF THE INVENTION

The present invention relates a novel system and method for person identification and personality assessment based on electroencephalography (EEG) signal. More particularly, this invention relates to a novel method of EEG recording and processing to map the inherent and unique properties of brain in the form of highly specific brain signature which is to be used as person identification and personality assessment. The present invention involves in creating a correlation matrix from EEG signals obtained in a fixed duration of time from the various locations of the scalp. The dynamics of the eigenvector together with the eigenvectors is studied to characterize brain function. Every individual has a specific rigidity in the dynamic behavior of their eigenvectors and that allows in creating a specific brain signature on such different brain activity more accurately and comprehensibly. This EEG based brain feature will be very specific and sensitive for individual.

In one aspect, the present invention is a novel EEG product which is composed of unique method of EEG recording and processing. The EEG product involves EEG recording by using spinal EEG and different scalp EEG electrodes. The EEG analysis is done by a unique process in which output data streams are taken together from a system like brain and the structure of their correlation matrix is studied through its eigenvector, eigenvalues, eigendirection and eigenspaces. The unique and persistent feature of the brain as brain signature is identified in this brain model which will be used as security key for any network or defense system.

In another aspect, the methodology of recording and processing EEG signals from multiple output data streams, comprising of the following steps:
  i. Performing EEG of individual scalp including suboccipital as well as spinal electrodes. The EEG will be done in normal, patients or criminals;
  ii. EEG is analyzed with different signal processing techniques like eigenvalues, eigenvectors, eigendirections, wavelet transform, fast fourier, compression technologies;
  iii. Functional modeling, aided with scalp bone transfer function characterization and functional imaging of brain is done by using said techniques.

This brain model is validated in different brain activity for creating specific brain signature so that identification of person can be done more effectively. The unique and persistent feature of the brain as brain signature is identified in this brain model which will be used as security key for any network or defense system. In addition to the same, personality assessment in various fields of application is also feasible.

Thus, the proposed system and method is capable of creating specific brain signature unique to an individual. The system and method provides for effective identification of a person. It further measures and assesses the personality and behavioural patterns for various fields of application. The system and method uses eigenvectors/eigenvalues, properties of inner product spaces and 4D visualization EEG signal's statistical, temporal and spectral properties to create the unique brain signature.

In another preferred embodiment of the present invention, a biometric kit based on the inventive concept of the present invention is proposed. The kit comprises at least a means for data input, a processing unit to process the data, and at least one output device to present the processed data as the result or assessment. The kit is capable of quickly identifying an individual to provide access to a security aspect. The kit uses eigenvectors/eigenvalues, properties of inner product spaces and 4D visualization EEG signal's statistical, temporal and spectral properties to interpret the brain signature.

The present invention will now be described more fully hereinafter with reference to the accompanying drawings in which a preferred embodiment of the invention is shown. This invention may, however, be embodied in many different forms and should not be construed as being limited to the embodiment set forth herein. Rather, the embodiment is provided so that this disclosure will be thorough, and will fully convey the scope of the invention to those skilled in the art.

Thus the present invention relates to providing a system and method using EEG signals, commonly known as brain-waves, for authenticating a user to give user access to a secure system. The systems gives three parameters that allows unique identification of an individual representing "brain signature", irrespective of what activity the person is engaged in or the kinds of thoughts that are appearing in his/her mind.

In an alternate embodiment of the present invention, a method of EEG based authentication and assessment of a user is suggested, the method comprising the steps of:
a. recording EEG signal data to obtain a brainwave pattern;
b. optionally grouping the signals obtained in step a. into at least two groups;
c. breaking the signal data into frames;
d. creating covariance matrix of each frame obtained in step c.;
e. computing eigenvectors and eigenvalues;
f. computing response vector covariance matrix from its eigenvectors and eigenvalues;
g. reducing the covariance matrix to three dimensional spherical coordinate parameters;
h. plotting the three dimensional parameters as a function of time to obtain four dimensional visualization of the EEG signals of step a.; and
i. observing distribution pattern of the parameters for deviation;
wherein any deviation in distribution pattern is indicator of abnormality.

Further, the signal data comprises at least 100 samples of each signal per second, and each group comprises plurality of signals. The frame comprises data consisting of at least 100 samples, of all the signals in each group taken separately. In a preferred mode, covariance matrix is a symmetric matrix constructed with the signals obtained and at least 100 samples for each signal. An eigenvector of a matrix is a vector which when multiplied by that matrix results in a scaled version of the original vector itself and the eigenvectors and eigenvalues are computed by equation $Ax_i = \lambda_i x_i$, where $x_i$ is one of the eigenvectors of A and $\lambda_i$ is its corresponding eigenvalue and wherein a n×n symmetric matrix gives n eigenvectors with corresponding n eigenvalues, n being any arbitrary integer. The three spherical coordinates comprises an angle a vector makes with the z-axis represented by $\rho$, an angle a vector makes with the x-axis represented by $\theta$, and the length of the vector represented by h.

The present invention will now be described more fully hereinafter with reference to the accompanying drawings in which a preferred embodiment of the invention is shown. This invention may, however, be embodied in many different forms and should not be construed as being limited to the embodiment set forth herein. Rather, the embodiment is provided so that this disclosure will be thorough, and will fully convey the scope of the invention to those skilled in the art.

The present invention provides an EEG based method to study and monitor functional aspects of the human brain in real time. Current technology is severely limited in being able to provide a decisive measure for every individual's neurological health by recording the functional behavior of the brain.

Figure 1:
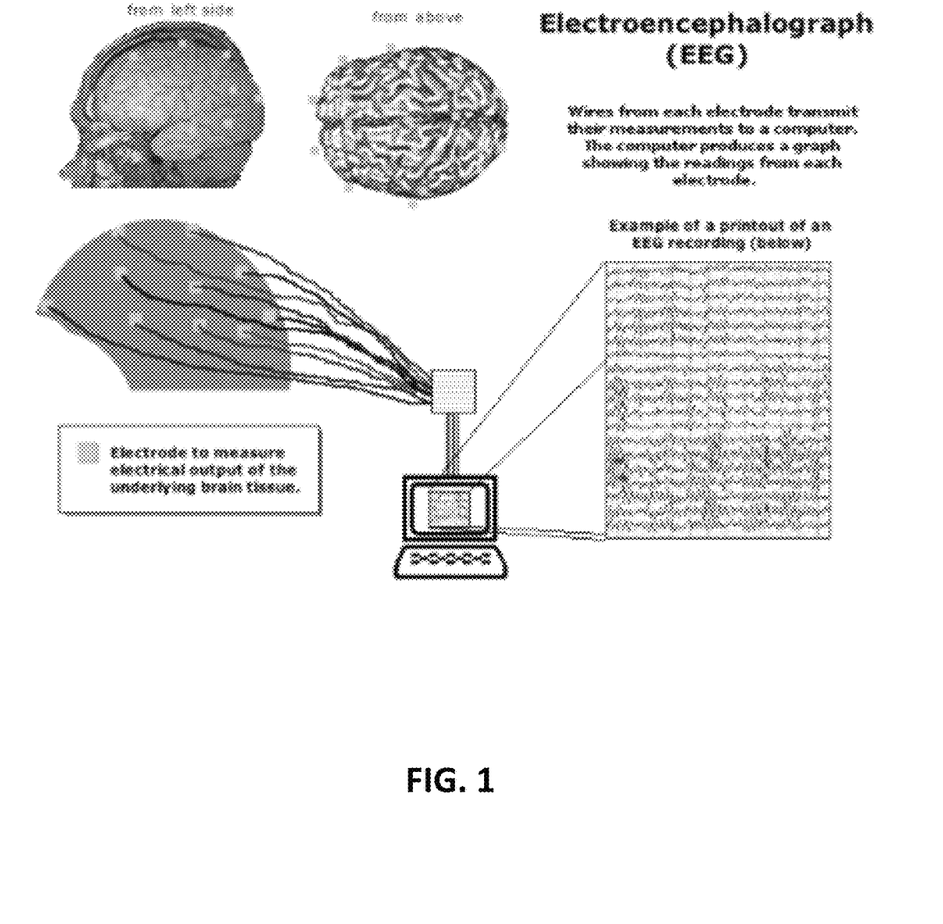
FIG. 1 shows a general overview of procedure of recording EEG signals.

As shown in FIG. 1, EEG signals appear on the entire area of the scalp of every person, from where they are recorded using multiple sensors. The proposed invention looks for a mathematical structure within the various signals recorded from different locations on the scalp and reports it via the 3 parameters. This mathematical structure is unique and all 3 parameters would match, within certain tolerance limits, only to a specific individual. The concept of this idea is explained in the following steps:
1. A set of sensors are placed on the scalp of a subject and signals emerging from the brain are recorded via an EEG device.
2. The system begins to analyse the EEG signals and starts giving values for three parameters each for left and right side of the brain, namely, $\rho$, $\theta$, and h, which represent the underlying mathematical structure of the signals appearing on the scalp.
3. The three parameters are plotted with time to give the novel 4 dimensional visualization of the entire EEG activity of the brain.
4. At the time of authentication the parameters are again measured and compared with previously stored values and the person is given access to the secure system if they match, within a pre-set tolerance limit.

The following minimum components are required for the foregoing steps to be completed.
1. EEG Scanner—Electroencephalography scanner is used to monitor and record brain activity. EEG measures the brain activity of various neurons and then reports them back to the system for further interpretation.
2. Algorithm based processing unit—This is a system that analyses the mathematical structure of the signals being received from a subject's scalp and, in real-time, produces parameters that are compared with previously recorded values to authenticate that individual.

Example 1

Sampling of EEG Data of Subject

Figure 2:
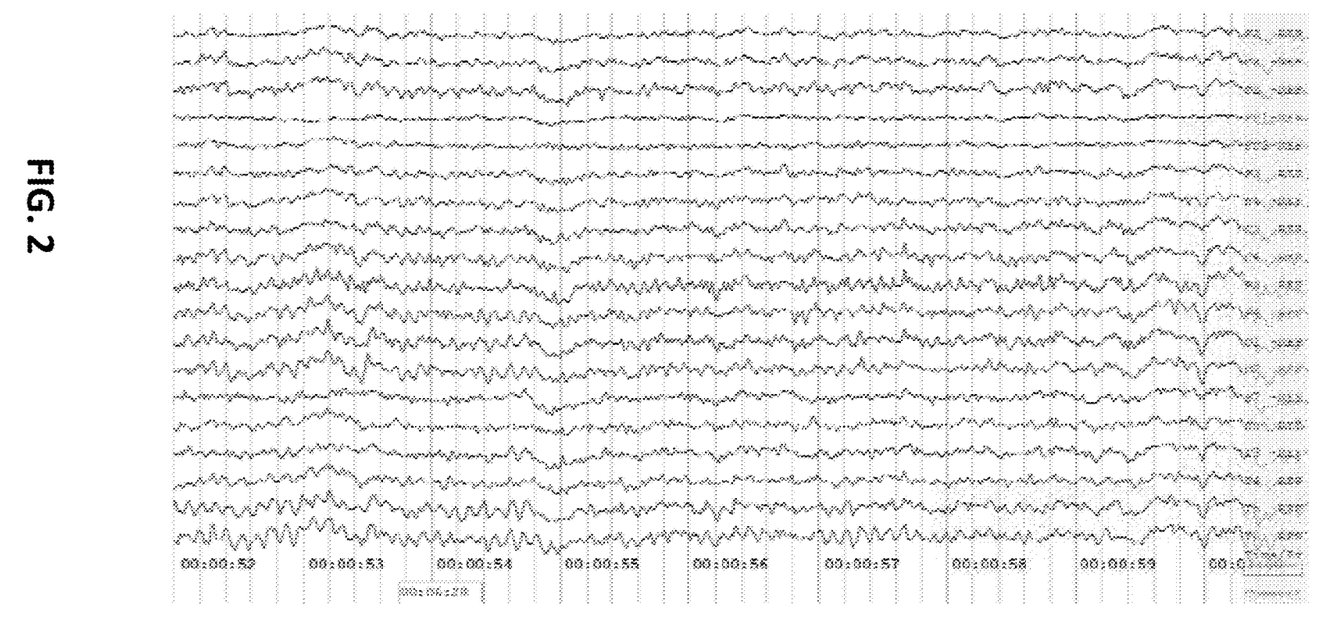
FIG. 2 depicts a sample of EEG signals recorded from a subject.

The internationally recognized 10-20 system is used to place the sensors on the scalp and record the EEG signals. FIG. 2 shows a sample of the EEG signals recorded from a subject. The name of each signal recorded is mentioned along with it on the extreme right of FIG. 2. First three signals, namely, Fz, Cz, Pz, lie along the line running at the centre of the scalp from the front to the back of the head. The signals ending with an odd number, for example, C3, lie on the left side of the scalp and those ending with an even number, for example, P4, lie on right side of the scalp.

Once the signals are recorded, they are separated into two groups, namely, left and right. The left group has all the signals that are obtained from the left side of the scalp, along with the signal Cz, and the right group has all the signals obtained from the right side of the scalp along with signal Cz. Therefore, each side has 9 signals each, listed as follows:

Left: Fp1, F7, F3, T3, C3, T5, P3, O1, Cz

Right: Fp2, F4, F8, C4, T4, P4, T6, O2, Cz

Figure 3:
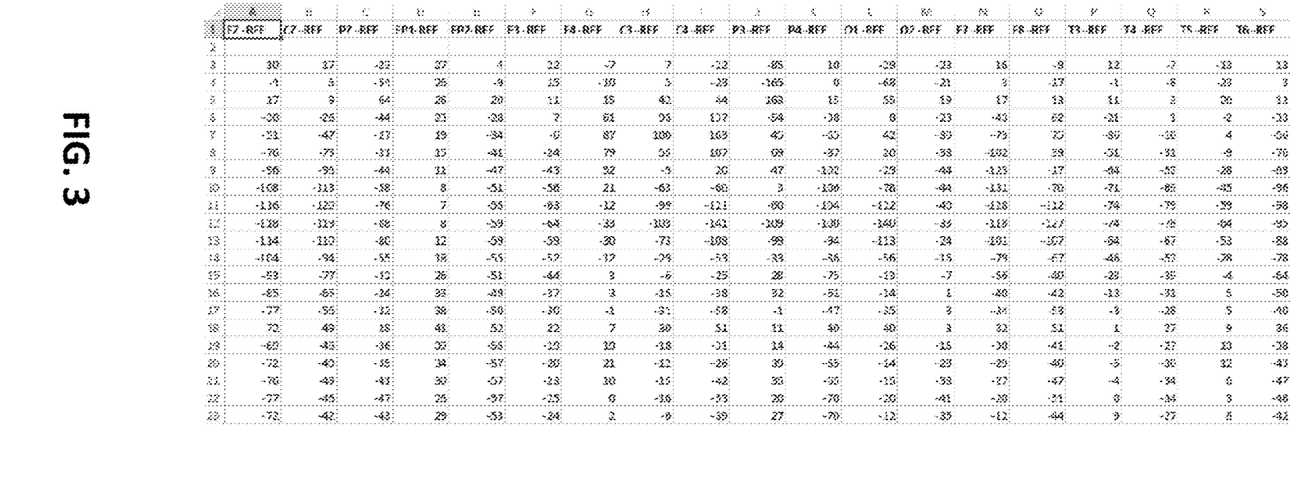
FIG. 3 shows the raw data of the signals represented in FIG. 2 that are used as input for the algorithm.

It does not matter in which order the signals are placed within the group. Once the left group and right groups have been created, the algorithm works independently of the order in which signals are put in each group. In general, any number of groups can be formed with any number of signals in them. In our study we have considered groups with number of signals that are powers of 3 and 4. This amounts to groups having 3, 4, 9, 16 etc. signals. The number of parameters generated in the end depend on whether the number of signals taken at the outset were a power of 3 or 4. If they are a power of 3, like 9 taken in each group in this embodiment, then there will be 3 parameters and 4 parameters will be produced when signals taken are a power of 4. Data is taken on an EEG machine that records 256 samples of each signal per second. FIG. 3 shows the raw data of the signals represented in FIG. 2 that are used as input for the algorithm. This entire data is then broken into 'frames' that are the size of 1 second each for both the left and the right group. In other words, 1 second worth of data, i.e., 256 samples, of all the 9 signals in each group is taken separately and called a frame. The process that follows now describes just one frame taken from one of the groups, but applies identically to all the frames of both groups.

Example 2

Constructing Covariance Matrix of Sample EEG Data of Subject

A covariance matrix is constructed with the 9 signals and 256 samples for each signal. FIG. 4 shows this covariance matrix. It is a symmetric 9×9 matrix that is populated with the covariance values of each signal with every other signal, computed using the 256 samples we have for all 9 signals. One can obtain the covariance between any two EEG signals by going to the row and column, with their respective names written next to each row and column of the matrix, and reading off that value from the matrix. For example, the covariance between F4 and C4 is 1301.435, and its location is at the $5^{th}$ column-$3^{rd}$ row and also, since the matrix is symmetric, $3^{rd}$ column-$5^{th}$ row.

With covariance matrix constructed we then proceed to compute its eigenvectors and eigenvalues. An eigenvector of a matrix is a vector which when multiplied by that matrix results in a scaled version of the original vector itself, i.e., $Ax_i = \lambda_i x_i$, where $x_i$ is one of the eigenvectors of A and $\lambda_i$ is its corresponding eigenvalue. A 9×9 symmetric matrix gives 9 eigenvectors with corresponding 9 eigenvalues. FIG. 5 show the 9 eigenvectors, with corresponding eigenvalues written on top, of the matrix in FIG. 4.

Example 3

Identifying Response Vector

Figure 6:
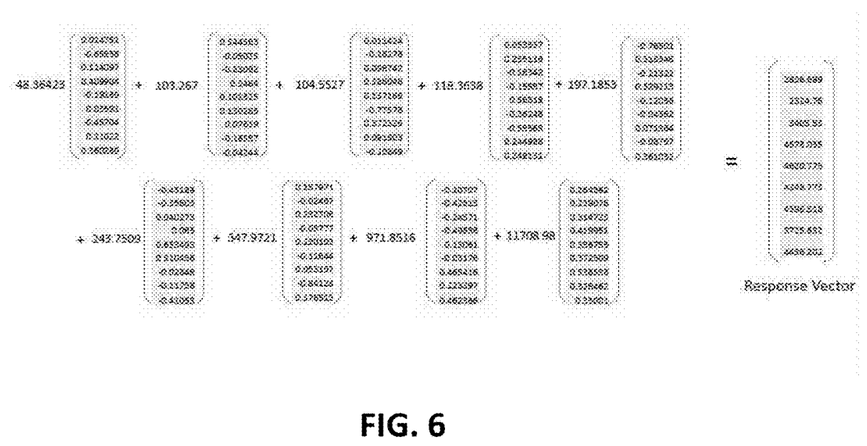
FIG. 6 shows the computation of the response vector of the covariance matrix in FIG. 4 from its eigenvectors and eigenvalues.
Figure 7:
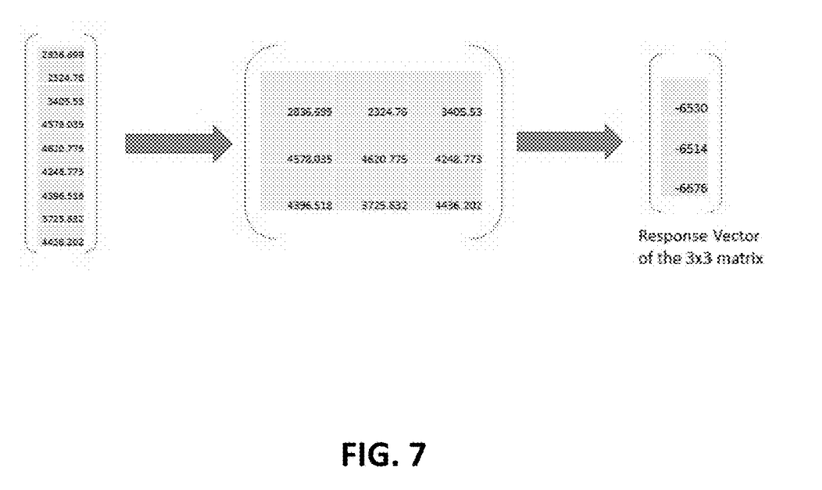
FIG. 7 depicts populated 3×3 matrix of rearrangement of values obtained in FIG. 6.
Figure 8:
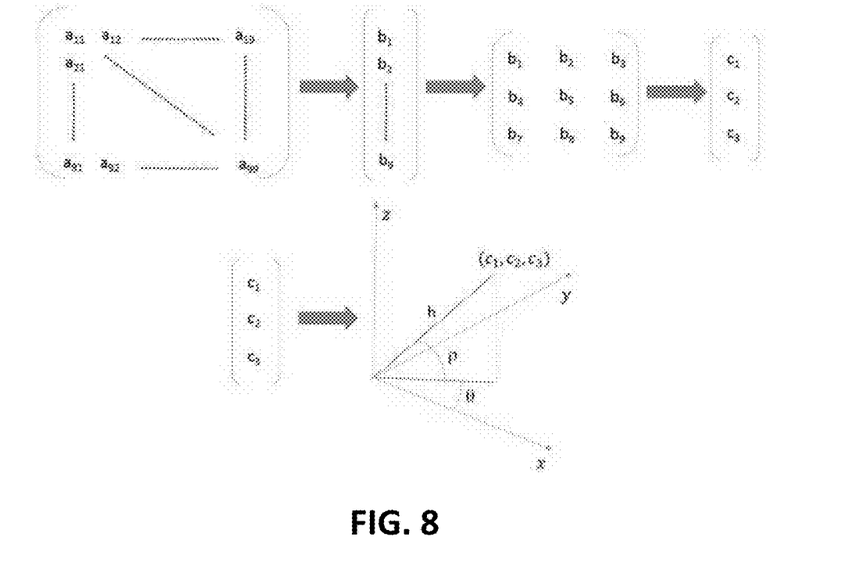
FIG. 8 shows process of taking a covariance matrix and reducing it to 3-dimensional spherical coordinates depicted in FIG. 7.

With all 9 eigenvectors and eigenvalues obtained, we first multiply each eigenvalue with its eigenvector and then add all the eigenvectors together, i.e., $\Sigma_i(\lambda_i v_i)$, to give what we call the response vector, A, of the covariance matrix. FIG. 6 shows the computation of the response vector of the covariance matrix in FIG. 4 from its eigenvectors and eigenvalues. This response vector is of the same size as the eigenvectors, i.e., 9×1, and its elements can be rearranged to populate a 3×3 matrix, as shown in FIG. 7. Using the process outlined above, we now compute the 3×1 response vector of this 3×3 matrix. Then a transformation from Cartesian coordinate system to Spherical coordinate system is performed for this 3×1 response vector. The 3×1 response vector shown in FIG. 7 is (−6530, 6514,−6676) in Cartesian coordinates. When transformed to spherical coordinates the vector becomes (−35.9,−135.1, 11385). The first two coordinates, $\rho$ and $\theta$, are the angles this vector makes with the z and the x-axis respectively and the last coordinate is the length of the vector denoted by h. This entire process of taking a covariance matrix and reducing it to 3-dimensional spherical coordinates is schematically depicted in FIG. 8.

Example 4

4D Visualization of EEG

Figure 9:
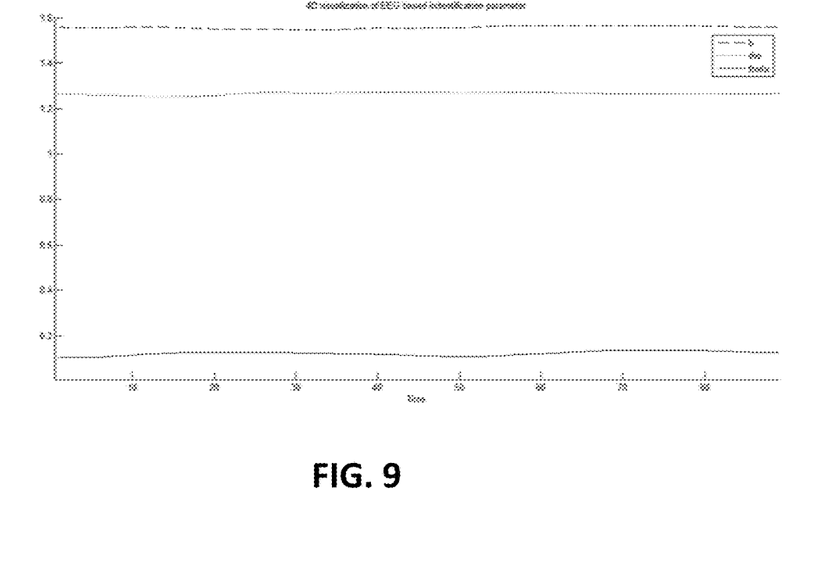
FIG. 9 shows the 4D visualization for the left group of a subject.

The above process is carried out for all the frames of 1 second duration, and three parameters for each frame are computed. These three parameters for each frame are plotted as a function of time to give the 4 dimensional visualization of the EEG. FIG. 9 shows the 4D visualization for the left group of a subject with 3 parameters as a function of time. We also analysed the distributions of the theta and rho parameter of EEG taken over a period of time and they too were specific to the individual person.

For security systems these parameters are recorded from any number of previously constructed groups of signals. In authentication process a subject's 4 dimensional EEG plots are generated acting as "brain signature" and compared with the previously recorded parameters. Access is provided only when the two match.

We claim:

1. An EEG based personality assessment system comprising:
    a means for sensing brainwaves of a user;
    a means for recording a pattern of the brainwaves of the user;
    a means for processing the recorded pattern, the means capable of performing an analysis of the brainwave pattern by giving values for three parameters each for left and right side of the brain, namely, $\rho$, $\theta$ and h, and plotting them with time resulting into a four dimensional visualization;
    a means for representing four dimensional visualization of the entire EEG activity of the user's brain obtained by the means for processing, as brain signature; and a means for securely storing the brain signature, wherein, multiple output data resulting from the pattern recorded are taken together and the structure of their correlation and higher-order statistics matrices are analyzed through its eignevalues, eigenvector, eigendirection and eigenspaces and other signal processing techniques like fast Fourier transform compression sensing, wavelet transform to obtain said four dimensional visualization.

2. The EEG based system as claimed in claim 1, wherein said means for sensing and recording brainwave pattern comprises an Electroencephalograph (EEG).

3. The EEG based system as claimed in claim 1, wherein the means for sensing and recording brainwave pattern includes spinal EEG and different scalp EEG electrodes.

4. The EEG based system as claimed in claim 1, wherein said means for processing pattern comprises a programmed processing unit.

5. The EEG based system as claimed in claim 1, wherein said brainwaves comprise EEG signals.

6. The EEG based system as claimed in claim 1, wherein said analysis further includes statistical, temporal and spectral property assessment of the EEG signals through four dimensional visualization of eigenvectors, eigenvalues, and properties of inner produce spaces plotted with time.

7. The EEG based system as claimed in claim 1, wherein the analysis further includes the step of creating correlation matrix from EEG signals obtained in a fixed duration of time from the various locations of the scalp.

8. The EEG based system as claimed in claim 1, wherein the means for representing four dimensional visualization of the entire EEG activity of the user's brain is an output device selected from the group comprising a printer, a visual output screen, an audio-visual output device or a combination thereof.

9. The EEG based system as claimed in claim 1, wherein the brain signature is unique to a user and is capable for being used as biometric authentication as well as a personality assessment tool.

10. A method of EEG based authentication and assessment of a user comprising the steps of:
   recording EEG signal data to obtain a brainwave pattern;
   optionally grouping the signals obtained in the recording step, into at least two groups;
   breaking the signal data into frames;
   creating covariance matrix of each frame obtain in the breaking step;
   computing eignenvectors and eigenvalues;
   computing response vector covariance matrix from its eigenvectors and eignevalues;
   reducing the covariance matrix to there dimensional spherical coordinate parameters;
   plotting the three dimensional parameters as a function of time to obtain four dimensional visualization as unique brain signature of the EEG signals of the recording step;
   storing the brain signature for subsequent references; and
   authenticating the user on the basis of stored brain signatures.

11. The method of EEG based authentication claimed in claim 10, wherein the signal data comprises at least 100 samples of each signal per second.

12. The method of EEG based authentication as claimed in claim 10, wherein each group comprises plurality of signals.

13. The method of EEG based authentication as claimed in claim 11, wherein a frame comprises data consisting of at least 100 samples, of all the signals in each group taken separately.

14. The method of EEC based authentication as claimed in claim 10, wherein covariance matrix is a symmetric matrix constructed with the signals and at least 100 samples for each signal.

15. The method of EEG based authentication as claimed in claim 10, wherein an eigenvector of a matrix is a vector which when multiplied by that matrix results in a scaled version of the original vector itself and the eigenvectors and eigenvalues are computed by equation $Ax_i = A_i X_i'$ where $X_i$ is on of the eignevectors of A and $A_i$ is its corresponding eigenvalue and wherein a n×n symmetric matrix give n eignevectors with corresponding n eigenvalues, n being any arbitrary integer.

16. The method of EEG based authentication is claimed in claim 10, wherein the three spherical coordinates comprises an angle a vector makes with the z-axis represented by $\rho$, an angle a vector makes with the x-axis represented by $\theta$, and the length of the vector represented by h.

17. The method of EEG based diagnosis as claimed in claim 10, wherein the brain signature is unique to a user and is capable of being used as biometric authentication as well as personality assessment tool.

* * * * *